United States Patent
Abdel Fattah et al.

(10) Patent No.: US 11,788,057 B2
(45) Date of Patent: Oct. 17, 2023

(54) 3D LABEL-FREE CONTACTLESS FORMATION OF CELLULAR STRUCTURES AND CO-CULTURES THROUGH DIAMAGNETOPHORESIS

(71) Applicant: McMaster University, Hamilton (CA)

(72) Inventors: Abdel Rahman Abdel Fattah, Etobicoke (CA); Rakesh Prasad Sahu, Hamilton (CA); Fei Geng, Hamilton (CA); Sarah Mishriki, Scarborough (CA); Elvira Meleca, Hamilton (CA); Ishwar K. Puri, Ancaster (CA); Suvojit Ghosh, Hamilton (CA)

(73) Assignee: McMaster University, Hamilton (CA)

( * ) Notice: Subject to any disclaimer, the term of this patent is extended or adjusted under 35 U.S.C. 154(b) by 994 days.

(21) Appl. No.: 16/178,172

(22) Filed: Nov. 1, 2018

(65) Prior Publication Data
US 2019/0127685 A1    May 2, 2019

Related U.S. Application Data

(60) Provisional application No. 62/580,088, filed on Nov. 1, 2017.

(51) Int. Cl.
C12N 5/00 (2006.01)
G01N 33/50 (2006.01)
C12Q 1/6876 (2018.01)

(52) U.S. Cl.
CPC ......... *C12N 5/0062* (2013.01); *C12Q 1/6876* (2013.01); *G01N 33/5032* (2013.01); *G01N 33/5082* (2013.01); *C12N 2513/00* (2013.01); *C12N 2527/00* (2013.01); *C12Q 2600/136* (2013.01)

(58) Field of Classification Search
CPC ............ C12N 2513/00; C12N 2527/00; C12N 2529/00; C12N 5/0062; C12Q 1/6876; C12Q 2600/136; G01N 33/5032; G01N 33/5082
See application file for complete search history.

(56) References Cited

U.S. PATENT DOCUMENTS

| | | | | |
|---|---|---|---|---|
| 2009/0137018 A1* | 5/2009 | Becker | ................. | C12N 5/0062 435/284.1 |
| 2014/0087440 A1* | 3/2014 | Becker | .................. | C12M 23/24 435/173.1 |

OTHER PUBLICATIONS

Tasoglu, S., and Demirci, U "Bioprinting for stem cell research." Trends In Biotechnology, 2013, 31(1): p. 10-19.

Mehrishi, J.N., and Bauer, J., "Electrophoresis of cells and the biological relevance of surface charge." Electrophoresis, 2002, 23(13): p. 1984-1994.

Korohoda, W., and Wilk, A., "Cell electrophoresis—a method for cell separation and research into cell surface properties." Cellular and Molecular Biology Letters, 2008, 13(2): p. 312-326.

Augustsson, P., et al., "Iso-acoustic focusing of cells for size-insensitive acousto-mechanical phenotyping." Nature Communications, 2016, 7.

Nordin, M., and Laurell, T., "Two-hundredfold volume concentration of dilute cell and particle suspensions using chip integrated multistage acoustophoresis." Lab on a Chip, 2012, 12(22): p. 4610-4616.

Xu, C., et al., "Study of Droplet Formation Process during Drop-on-Demand Inkjetting of Living Cell-Laden Bioink." Langmuir, 2014, 30(30): p. 9130-9138.

Kimura, T., et al., "Micropatterning of cells using modulated magnetic fields." Langmuir, 2005, 21(3): p. 830-832.

Winkleman, A., et al., "A magnetic trap for living cells suspended in a paramagnetic buffer." Applied Physics Letters, 2004, 85(12): p. 2411-2413.

Durmus, N.G., et al., "Magnetic levitation of single cells." Proceedings of the National Academy of Sciences, 2015, 112(28): p. E3661-E3668.

Akiyama, Y., and Morishima, K., "Label-free cell aggregate formation based on the magneto-Archimedes effect." Applied Physics Letters, 2011, 98(16): p. 163702.

Fattah, A.R.A., et al., "High Gradient Magnetic Field Microstructures for Magnetophoretic Cell Separation." Journal of Chromatography B, 2016A, 1027; p. 194-199.

Shen, F., et al., "Label-free cell separation using a tunable magnetophoretic repulsion force." Analytical Chemistry, 2012, 84(7): p. 3075-3081.

Melville, D., et al., "Fractionation of blood components using high gradient magnetic separation." IEEE Transactions on Magnetics, 1982, 18(6): p. 1680-1685.

Melville, D., et al., "Direct magnetic separation of red cells from whole blood." Nature, 1975, 255: p. 706.

(Continued)

*Primary Examiner* — Blaine Lankford
(74) *Attorney, Agent, or Firm* — BERESKIN & PARR LLP/ S.E.N.C.R.L. s.r.l; Tonino Rosario Orsi

(57) ABSTRACT

A novel macroscale, contactless, label-free method to print in situ three-dimensional (3D) particle assemblies of different morphologies and sizes is demonstrated using non-adherent (blood) and adherent (MCF-7 and HUVEC) cells. This method of manipulating particles such as cells or biological moleules does not necessarily require the use of nozzles that can contaminate the cell suspension, or to which cells can adhere. Instead, the intrinsic diamagnetic properties of particles such as cells are used to magnetically manipulate them in situ in a nontoxic paramagnetic medium, creating various shapes such as (a) rectangular bar, (b) three-pointed star, and (c) spheroids of varying sizes. A normal distribution of 3D cell structures is produced when formed through magnetic assembly. The use of this method in co-culturing of different cell lines is also demonstrated. The technique is envisioned to be transferable to other cell lines or diamagnetic biological molecules, with potential applications in tissue engineering, medical diagnostics and drug screening.

22 Claims, 13 Drawing Sheets

(56) References Cited

OTHER PUBLICATIONS

Morgunov, R.B., et al., "Thermally-induced paramagnetism of spiropyrane iodides." New Journal of Chemistry, 2009, 33(6): p. 1374-1379.
Tsutsui, H., and C.-M. Ho, "Cell separation by non-inertial force fields in microfluidic systems." Mechanics Research Communications, 2009, 36(1): p. 92-103.
Graham, M., "Comparison of volume and surface mechanisms for magnetic filtration of blood cells." Le Journal de Physique Colloques, 1984, 45(C1): p. C1-779-C1-784.
Mishriki, S., et al., "Rapid Magnetic 3D Printing of Cellular Structures with MCF-7 Cell Inks." Research, Feb. 4, 2019; 9854593, 13 pages.
Fattah, A.R.A., et al., "Gadopentatic acid affects in vitro proliferation and doxorubicin response in human breast adenocarcinoma cells." BioMetals, 2018A, 31: 605-616.
Fattah, A.R.A., et al., "3D cellular structures and co-cultures formed through the contactless magnetic manipulation of cells on adherent surfaces." Biomaterials Science, 2018B; 6(3): 683-694.
Fattah, A.R.A., et al., "In Situ 3D Label-Free Contactless Bioprinting of Cells through Diamagnetophoresis." ACS Biomaterials Science & Engineering, 2016B; 2(12): 2133-8.

\* cited by examiner

A

B

3D LABEL-FREE CONTACTLESS FORMATION OF CELLULAR STRUCTURES AND CO-CULTURES THROUGH DIAMAGNETOPHORESIS

RELATED APPLICATIONS

This application claims the benefit of priority to U.S. Provisional Application No. 62/580,088 filed Nov. 1, 2017, the entire contents of which are hereby incorporated by reference.

FIELD

The present disclosure pertains to the field of tissue engineering, medical diagnostics and drug screening. More particularly, the present disclosure relates to the technical field of contactless 3D printing of particles such as cells using diamagnetophoresis.

BACKGROUND

Separation, concentration and overall manipulation of cells has been of significant interest in cell biological assays and medical diagnostics [1-4]. Specifically, manipulation of cells into three-dimensional (3D) cultures have gained attention due to such cell assemblies more closely mimicking physiological conditions compared to monolayered cell culture. Printing 3D cell assemblies and patterns can further simplify tissue engineering, cell-on-chip devices and drug screening applications.

A typical method to create 3D cell structures utilizes the hanging drop technique, which limits assemblies to spherical geometries of relatively small sizes [1]. Other alternative methods include label-free manipulation of cells, for example electrophoresis [2, 3], and acoustophoresis [4, 5]. Such methods employ external fields, subjecting cells to body forces thereby serving several applications such as continuous separation of cells from a mixture within a microfluidic channel with high concentration and throughput. However, while electrophoresis suffers from laborious electrode fabrication, microfluidic design and assemblies, acoustophoresis is restricted to concentrate cells at the pressure nodes along the length of a microchannel. While 3D bioprinters deposit cells or their aggregates in layers with spatial precision [6], they are relatively slow, expensive, and use nozzles, the surfaces of which can introduce contamination or where cells can adhere and clog the flow. Moreover, scaffolds such as hydrogels are an essential constituent to form 3D constructs which limits the bioprinting process due to resolution, cytotoxicity, solidificability and practicality. None of the active methods mentioned above had been used to manipulate and aggregate cells into 3D assemblies of different shapes and sizes without the need of an external scaffold. The recent and urgent need of studying the complex behavior of cell assemblies mimicking actual tissues in the field of tissue engineering and drug screening motivates the present work.

Diamagnetophoresis is a method of suspending cells within a paramagnetic buffer and application of external magnetic field allows the cells to move towards the region of lower magnetic field strength. 3D cell aggregates of different shapes and sizes could be formed in a controlled way using the process of diamagnetophoresis. However, previous applications of diamagnetophoresis to manipulate and pattern cells have employed high gradient magnetic field microstructures [7-9], which restrict the method to micron size cell assemblies that rely on an externally generated fluid flow to transport cells from high to low magnetic field strength regions. Attempts have been made to create 3D structures using diamagnetophoresis for adherent cells suspended in paramagnetic media [10]. However, the method is restricted to spherical geometry only. There is a need for non-invasive and rapid formation of 3D cellular structures of controlled geometry that closely resembles the in vivo conditions of different tissues.

SUMMARY

As set out in the Examples, the inventors disclose herein a technique that magnetically manipulates diamagnetic particles such as cells in a nontoxic paramagnetic gadolinium solution of Gadopentatic acid (Gd-DTPA) and PBS medium to print in situ label-free 3D cell assemblies of various geometries. The method is rapid, controlled and utilizes the intrinsic magnetic properties of cells to print in situ 3D cell assemblies through a contactless method. The paramagnetic buffer is mixed into a solid-fluid suspension, leading to a difference between the magnetic susceptibilities of the solid and its surrounding medium, which induces differential magnetic forces on the mixture constituents [11-13]. When an external magnetic field is applied on such a cell-medium system, a cell behaves as a diamagnetic material that migrates towards the region of lower magnetic field strength. Using non-adherent whole blood, data is presented showing the first realization of a novel macroscale method to print in situ cell assemblies of different sizes and morphologies without introducing external flows or surfaces. Such cell manipulation is extended to adherent cell lines using human breast cancer MCF-7 cells, and their patterning on tissue culture treated and ultra-low adhesion surfaces. Co-culturing of different cell lines may also be facilitated using this technique. The methods described herein do not necessarily require require nozzles, additional surfaces, electrodes, or microfluidic devices. Rather, diamagnetophoretic printing is an in situ method that requires only cells, an appropriate paramagnetic medium and a suitable magnetic field. The method described herein for preparing 3D cell constructs and co-culturing of cells is compatible with the cells, simple, rapid, economic and safe.

Accordingly, in one embodiment there is provided a method of forming an assembly of particles, the method comprising:
  combining a plurality of diamagnetic particles with a paramagnetic agent to form a suspension of particles in a paramagnetic solution; and
  applying an external magnetic field to the suspension of particles in the paramagnetic solution to form one or more regions of lower magnetic field strength,
  wherein particles in the suspension move towards the one or more regions of lower magnetic field strength in the paramagnetic solution forming the assembly of particles.

In one embodiment, the diamagnetic particles are cells. In one embodiment, the diamagnetic particles comprise or consist of one or more biological molecules such as proteins, carbohydrates, lipids, and/or nucleic acids.

In one embodiment, the external magnetic field may be generated by an array of two or more magnets, optionally permanent magnets or electromagnets. In one embodiment, the assembly of particles forms a 3-dimensional structure or aggregate. As described herein, various 3-dimensional structures may be formed by controlling the external magnetic field applied to a suspension of particles in a paramagnetic solution. In one embodiment, the 3-dimensional structure is a spheroid or sphere. For example, in one embodiment the method comprises applying an external magnetic field to a suspension of cells in a receptacle using an array comprising 4 magnets in a 2×2 array in a N-S-N-S orientation and the resulting cell assembly is a sphere or spheroid.

In one embodiment, the suspension of diamagnetic particles in the paramagnetic solution are contained in a receptacle such as, but not limited to, a cell culture plate or a microtiter plate. In one embodiment, the receptacle comprises a flat surface in contact with the suspension of particles. Optionally, one or more surfaces of the receptacle in contact with the suspension of cells are treated to promote or inhibit cell adhesion.

In one embodiment, the paramagnetic agent is a Gadolinium-based contrasting agent. For example, in one embodiment the paramagnetic agent is Gadolinium-diethylenetriamine penta-acetic acid (Gd-DTPA). In one embodiment, the paramagnetic solution comprises phosphate buffered saline or cell culture media.

The particles assemblies formed using the embodiments described herein are useful for a number of practical applications. For example, in one embodiment there is provided a method of screening a compound for a biological activity, the method comprising forming an assembly of cells according to a method as described herein, contacting the assembly of cells with the compound, and detecting a change in the biological activity of the assembly of cells in contact with the compound. In one embodiment, the methods and products described herein may be used for generating assemblies of cells for use in high throughput screening assays. For example, in one embodiment, the assemblies of cells are spheres or spheroids of a predetermined and consistent size.

Also provided are products and kits as described herein useful for forming an assembly of particles using a paramagnetic agent. In one embodiment, there is provided a kit comprising a paramagnetic agent, optionally Gd-DTPA, and an array of two or more magnets for applying an external magnetic field to a receptacle, optionally wherein the receptacle is a cell culture plate or a micro titer plate.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which.

DETAILED DESCRIPTION

I. Definitions

Figure 1:
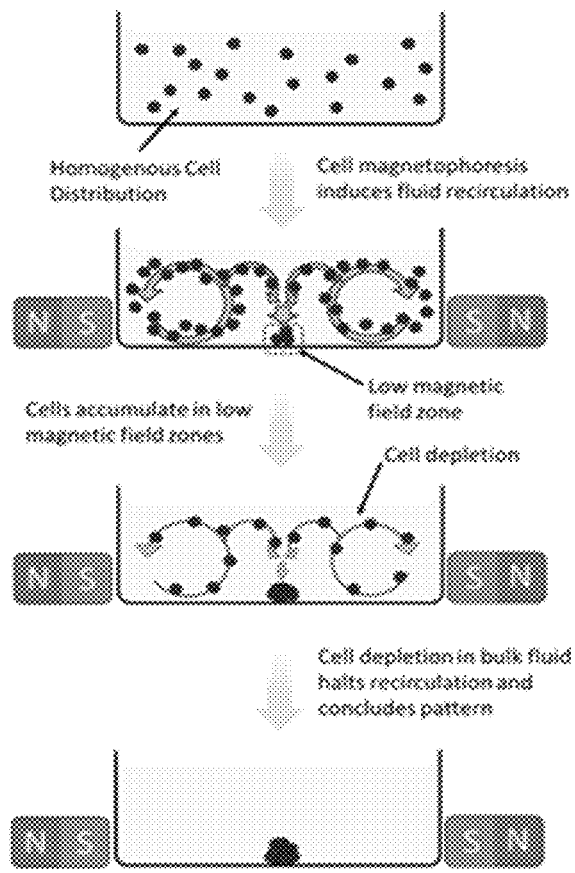
FIG. 1 shows the schematic of the recirculation of cells in a paramagnetic buffer solution and subjected to an external magnetic field.

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a cell" or "3D aggregate" should be understood to present certain aspects with one substance or two or more additional substances.

The term "and/or" as used herein means that the listed items are present, or used, individually or in combination. In effect, this term means that "at least one of" or "one or more" of the listed items is used or present.

In one aspect, there is provided a method of forming an assembly of particles. In one embodiment, the particles are cells. In one embodiment, the particles are diamagnetic biological molecules. In one embodiment, the particles are unicellular organisms such as bacteria or viruses.

As used herein, an "assembly of particles" refers to a sample volume comprising a higher concentration of particles relative to a surrounding volume. Optionally an assembly of cells may form an aggregate or structure wherein intercellular forces maintain the assembly of cells in the absence of paramagnetic solution and a magnetic field.

In one embodiment, the method comprises combining a plurality of particles with a paramagnetic agent to form a suspension of particles in a paramagnetic solution and applying an external magnetic field to the suspension of particles in the paramagnetic solution to form one or more regions of lower magnetic field strength.

Diamagnetic particles in the suspension will move in response to the magnetic field towards the one or more regions of lower magnetic field strength in the paramagnetic solution, thereby forming the assembly of particles. In one embodiment, the assembly of particles forms a 3-dimensional structure or aggregate.

As set out in the Examples and without being limited by theory, the formation of 3D structures assisted by diamagnetophoresis is due to the interplay of a) fluid recirculation within the volume of the fluid and b) Fm minimum (the magnetic field minimum). The fluid recirculation is initiated due to the difference in susceptibility of the liquid and the particles suspended in it and the shape of the region of lower magnetic field strength (such as Fm minimum or a minimum potential well) depends on the orientation and shape of the magnets. A person of skill in the art can model the magnetic field by changing the orientation and shape of the magnets. The model will give the magnetic lines of force and a knowledge of the shape of the minimum potential well where the cells will aggregate and form a 3D structure.

Figure 4:
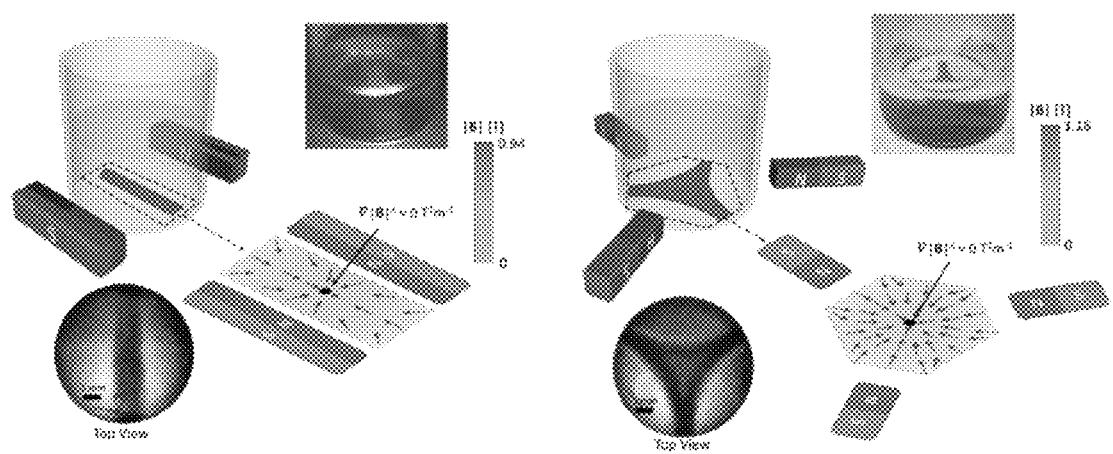
FIG. 4 shows two different 3D morphologies formed using blood cells by appropriate organization of the magnetic field.

Accordingly, different types or shapes assemblies may be formed using the embodiments described herein. For example, as shown in FIG. 4A, a bar assembly of cells or particles may be formed using a pair of magnets with 180° pole angles placed side by side. As shown in FIG. 4B, a three-pointed star morphology may be formed using three magnets with 120° pole angles places next to each other. Various other assemblies such as polyhedrons and/or curved shapes may be formed by applying an external magnetic field to a suspension of particles or cells in a paramagnetic solution such as by using an array of two or more magnets.

Figure 5:
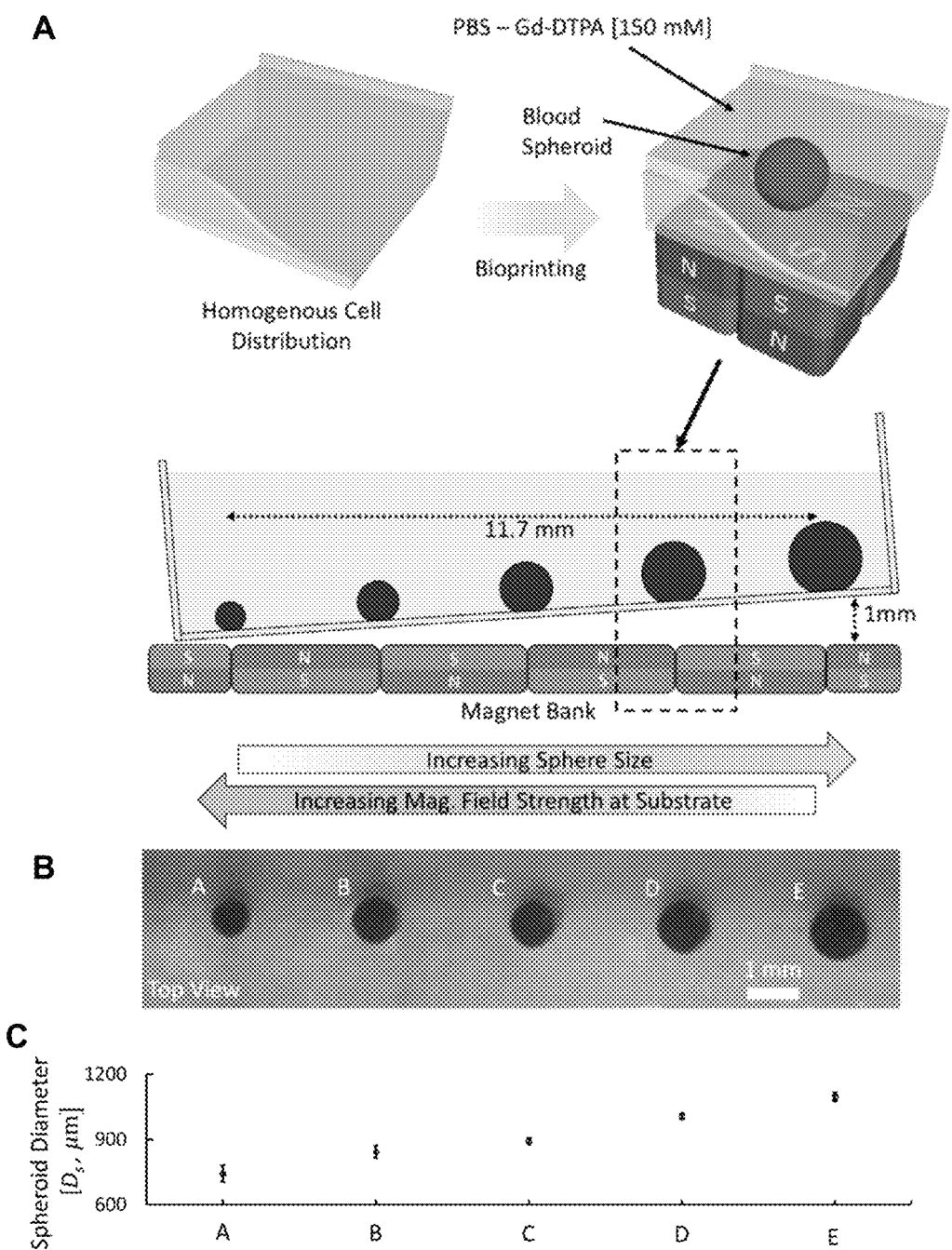
FIG. 5 shows the formation of spheroids of different sizes.

The embodiments described herein are also useful for forming spherical assemblies of particles such as spheres or spheroids. As shown in FIG. 5, spheroids of various sizes can readily be formed using a magnet bank or array comprising 2×2 arrays of 4 magnets wherein the poles of adjacent magnets alternate in the array such as in a N-S-N-S orientation. In one embodiment, the array comprises 4 or more magnets in a N-S-N-S orientiation.

In one embodiment, the external magnetic field is generated by an array of two or more magnets. In one embodiment, the magnet is a permanent magnet (such as a neodymium magnet) or an electromagnet.

In one embodiment, the suspension of particles in the paramagnetic solution may be contained in a receptacle. Examples of receptacles suitable for use with the embodiments describes herein include cell culture plates and/or micro titer plates such as standard 96 well or 384 well microtiter plates. In one embodiment, the receptacle comprises a flat surface in contact with a sample or solution contained in the receptacle.

The surface of the receptacle in contact with the suspension may be treated to promote or inhibit (reduce) the adhesion of cells and/or particles to the walls of the receptacle.

Optionally, one or more magnets used for generating an external magnetic field may be integral to the receptacle. In another embodiment, the magnets used for generating the external magnetic field may be positioned on a reusable array that is adapted for receiving a receptacle such as a standard 96 well or 384 well microtiter plate. Optionally, such an array may be generated by forming magnetic microstructures using lithographic and/or microfabrication techniques In one embodiment, the paramagnetic agent comprises a Gadolinium based salt or contrasting agent, optionally Gadolinium-diethylenetriamine penta-acetic acid (Gd-DTPA). The paramagnetic agent may be prepared in a solution that is suitable for the particles to be formed in the assembly. For example, in one embodiment, the particles are cells and the paramagnetic agent in prepared in a solution comprising Gd-DTPA mixed with phosphate-buffered saline or cell culture media. A skilled person would readily be able to identify other buffers or culture media suitable for use with the embodiments described herein depending on the type of cells to be assembled and/or cultured.

In one embodiment, the concentration of Gd-DTPA in the paramagnetic solution is between about 0.001 M to 0.2 M or between about 0.001 and 0.5 M. The concentration of paramagnetic agent used in the methods described herein may be higher or lower depending on the nature of the conditions and the particles to be assembled. As set out in the Examples, the concentration of the paramagnetic agent required to form an assembly will depend on factors such time, the size of the particles, and the difference in magnetic susceptibility between the diamagnetic particles and the paramagnetic solution.

In one embodiment, the method comprises applying the external magnetic field to the suspension of particles in the paramagnetic solution for at least 30 minutes, 1 hour, 2 hours, 4 hours, 5 hours, 6 hours, 8 hours, 12 hours, or at least 24 hours. In one embodiment, the method comprises applying the external magnetic field to the suspension of particles in the paramagnetic solution for between about 4 hours and 8 hours. In one embodiment, the method comprises applying the external magnetic field to the suspension of particles in the paramagnetic solution for less than 10 hours, less than 8 hours, less than 6 hours, or less than 4 hours.

In one embodiment, the method comprises replacing all of part of the paramagnetic solution with a solution that does not contain the paramagnetic agent after the assembly of the particles is sufficient or complete, such as following the formation of a desired 3D structure. For example, in one embodiment the method comprises replacing the paramagnetic solution with a cell culture media suitable for culturing the assembly of cells that does not contain the paramagnetic agent.

The embodiments described herein may be used to assembly various cell types. In one embodiment, the cells are animal cells or plant cells. In one embodiment, the cells are from a cell line. In one embodiment, the cells are from a biological sample such as a sample taken from a patient. In one embodiment, the cells are adherent cells. In one embodiment, the cells are non-adherent cells or semi-adherent cells.

Optionally, the cells are dissociated or treated to remove contaminants prior to forming assemblies using the methods described herein.

Optionally, the methods described herein may be used to form assemblies comprising different types of particles or a homogenous assembly of particles. In one embodiment, the particles are cells of the same type or of different types.

The methods described herein may be repeated to form assemblies of particles of varying complexity. For example, in one embodiment the particles or cells form a first aggregate in a receptacle and the method further comprises adding a second plurality of particles cells to the receptacle and applying an external magnetic field to a suspension comprising the second plurality of particles or cells in the paramagnetic solution to form a second aggregate of cells. In one embodiment, the first aggregate and the second aggregate are spatially resolved and/or distinct. Alternatively, the first aggregate and second aggregate may form a 3-dimensional structure.

As demonstrated in the Examples, the methods described herein may be used to form assemblies in the presence of pre-existing cellular structures such as a monolayer of adherent cells. In one embodiment, the plurality of cells are in a receptacle comprising an adherent cell culture, optionally a monolayer of cells on a bottom surface of the receptacle. The method described herein may therefore be used to form assemblies adjacent to an existing structure of cells in a receptacle.

In one aspect of the disclosure, there is provided screening assays that use the assemblies of cells as described herein. In one embodiment, the screening assays are high throughput screening assays. The term "high throughput screening" as used herein refers to automated in vitro testing of the effect of compounds or conditions on cells and such screening is typically performed with the aid of computer or robot-controlled processes. As used herein, the term "compound" includes, without limitation, chemicals, pharmacological agents, small organic molecules, biomolecules, polypeptides, proteins, antibodies, sugars, polysaccharides, polynucleotides, cells, or combinations thereof. Such a compound may be a naturally-occurring product or a synthetic product.

In one embodiment, there is provided a method of screening a compound for a biological activity using assemblies of cells as described herein. In one embodiment, the method comprises:

forming an assembly of cells as described herein;
contacting the assembly of cells with the compound; and
detecting an effect of the compound on the assembly of cells in contact with the compound.

As used herein the phrase "screening a compound for a biological activity" refers to identifying or testing a compound with respect to its physiological or pharmacological effects on the normal or abnormal biochemical function of one or more cells. As used herein the phrase "biological activity" includes but is not limited to cell toxicity (cytotoxicity), apoptosis, cell death, signal transduction, cell signaling, cell differentiation, loss of pluripotency, cell growth, or anticancer activity.

In one aspect, the methods described herein comprise screening a compound for biological activity by detecting an effect of the compound on an assembly of cells. In one embodiment, the effect is indicative of biological activity of the compound. In one embodiment, "detecting an effect" comprises monitoring or determining cell size or morphology, expression of cell markers, the emergence of cell types or the biochemical make-up of the cell with the assembly of cells. For example, in one embodiment "detecting an effect" includes, but is not limited to, using methods such as immunohistochemistry ELISA, reporter genes, PCR or RT-PCR, fluorescent lables, cytometric bead arrays, DNA arrays, flow cytometry or optical analysis to detect the effect of a compound on an assembly of cells.

In one embodiment, there is provided a kit comprising a paramagnetic agent, optionally Gd-DTPA, and an array of two or more magnets for applying an external magnetic field to a receptacle. In one embodiment, the receptacle is a cell culture plate or a micro titer plate. In one embodiment, the array is integral to a receptacle or is a separate product such as a template for applying an external magnetic field to a receptacle.

For example, in one embodiment the kit comprises a template array comprises a plurality of magnets positioned for applying a magnetic field to a series of wells in a micro-titer plate. Optionally, the magnets are positioned in order to generate a magnetic field that would form a predetermined assembly or structure such as a sphere as described herein.

EXAMPLES

Formation of Cellular Structures Through Diamagnetophoresis

Gadopentatic acid was mixed with phosphate-buffered saline (PBS) and the whole blood cells were suspended in the paramagnetic buffer of Gd-DTPA solution. The difference in magnetic susceptibilities of the cells and the medium results in a differential force that the cells experience in situ, and they move towards regions of lower magnetic field strength, $B_{low}$. While some cells settle immediately, others are transported away through inertia, but the differential force returns these escaped cells back towards $B_{low}$. This back and forth cell motion induces fluid recirculation through momentum transfer between the cells and fluid, settling an increasing number of cells around $B_{low}$ over time with an equivalent depletion elsewhere in the medium. The recirculation eventually ceases, as shown in FIG. 1. Additionally, after assembly the cells are still subjected to varying magnetic fields, which is anticipated to induce mechanical stresses, mimicking those in physiological conditions. This may add to the degree of similarity between in vitro and in vivo experimentation.

The magnetic force on a cell [14-16], $F_M$ is expressed as $$F_m = ((\chi_c - \chi_m)/2\mu_o) V_c \nabla |B|^2 \quad (1.1)$$

where $\chi_c$ and $\chi_m$ denote the magnetic susceptibilities of the cell and fluid medium, $V_c$ and $\mu_0$ the cell volume and permeability of free space, and $\nabla |B|$ the magnetic field gradient. Hence, $F_M$ depends on the (1) difference in the magnetic susceptibilities between the cell and fluid medium, (2) cell volume, and (3) magnetic field gradient. Assuming that all cells are spherical, the drag force that they experience due to Stokes flow is $F_d = 6\pi\eta UR$, where h denotes the medium viscosity, U cell velocity, and R cell radius. This force can be appropriately modified for cells with other sizes and morphologies. Since cells have negligible inertia, $F_d = F_m$. Hence, the terminal velocity of a cell with with $V_c = (4/3)\pi R^3$ is, $$U = 2R^2 f_c/(9\eta) \quad (1.2)$$

where $f_c$, the magnetic body force on the cell is given as, $$f_c = ((\chi_c - \chi_m)/2\mu_o)\nabla|B|^2 \qquad (1.3)$$

Assuming a strong paramagnetic host medium, $(\chi_c - \chi_m) \approx -\chi_m$ $$U = -((R^2\chi_m)/9\eta\mu_o)\nabla|B|^2 \text{ i.e.,} \qquad (1.4)$$

the terminal velocity scales with $R^2$. The printing time and induced convection depend on U. Hence larger cells undergo more rapid magnetophoresis and print in situ patterns faster than their smaller counterparts. Furthermore, it is anticipated that since adherent cells form clusters, their larger equivalent radius would improve the print speed over that when non-adherent cells that have smaller sizes are used.

Magnetic Susceptibility Measurement of Gd-DTPA and PBS Solution

Figure 2:
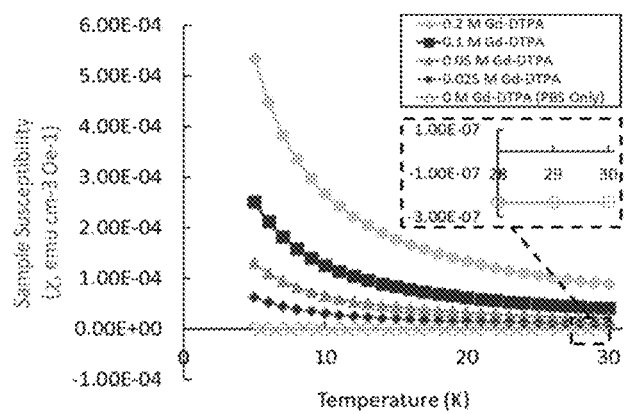
FIG. 2 shows the susceptibility of the Gd-DTPA for different concentrations in PBS.

Dissolving gadopentatic acid (Gd-DTPA) in phosphate-buffered saline (PBS) imparts paramagnetic properties to the solution. Four solutions at 300 K were created with different Gd-DTPA concentrations and loaded 50 µL of each sample in a size 5 capsule to conduct superconducting quantum interference device (SQUID) measurements. For reference, a sample containing only PBS was also examined. The SQUID performed a temperature sweep from 5 to 30 K that provided 25 measurements, one magnetic moment measurement (emu) per degree, with a 1 kOe field. The paramagnetic susceptibility was calculated using the inverse Curie-Weiss law. This susceptibility increases with increasing Gd-DTPA concentration, as shown in FIG. 2, where $\chi_m = 7.00 \times 10^{-6}$, $2.33 \times 10^{-6}$, $1.33 \times 10^{-6}$, and $1.00 \times 10^{-6}$ for the 0.2 M, 0.1 M, 0.05 M and 0.025 M Gd-DTPA concentrations. The PBS sample exhibits typical diamagnetic response with a negative susceptibility $\chi_m = -2.32 \times 10^{-7}$ and no temperature dependence. Therefore, a buffer solution can be tailored by varying the added amount of a paramagnetic salt, which alters the diamagnetic response of cells. This variation can be controlled to print in situ macroscopic cellular structures.

Viability Tests of Blood Cells

Figure 3:
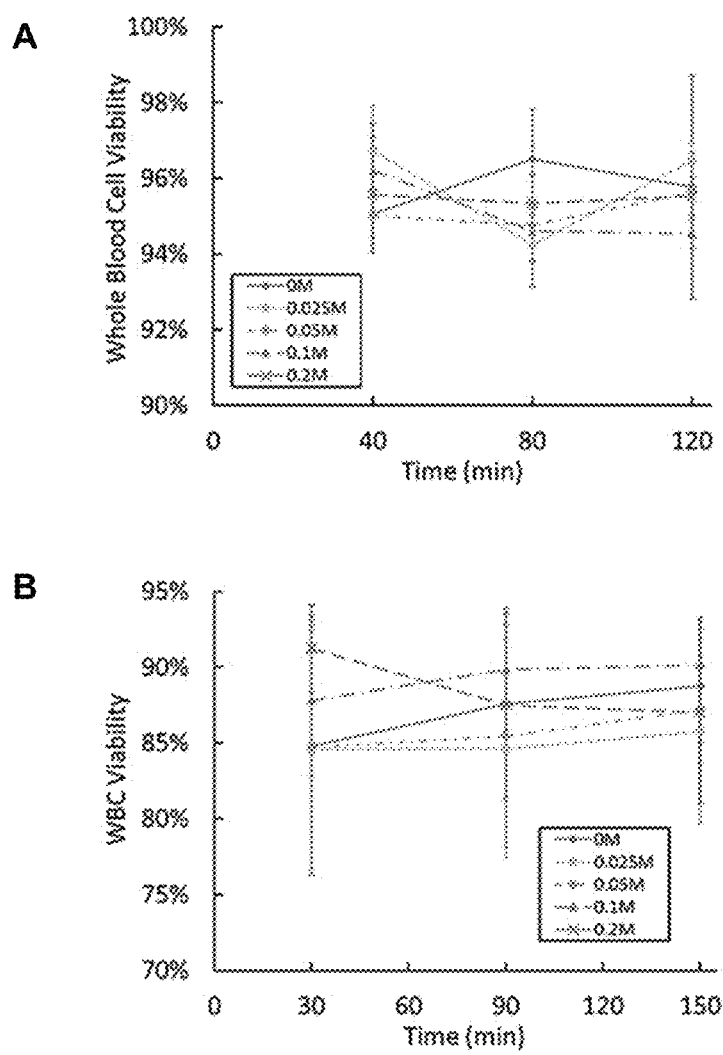
FIG. 3 shows the viability of whole blood cells and white blood cells at different concentration of Gd-DTPA.

The viability of whole human blood was first investigated to examine Gd-DTPA toxicity towards them for the four aforementioned concentrations. The pH of the solutions was initially acidic ~1.7, but was adjusted to the isotonic value of ~pH 7.4 with sodium hydroxide and hydrochloric acid. The whole blood was first suspended in each Gd-DTPA solution and incubated at standard conditions (37° C. and 5% $CO_2$) for 40, 80 and 120 mins, along with another sample that contained the blood in a reference PBS-only control. Viability of whole blood was examined using a Nexcelom Cellometer Auto 2000 Cell Viability Counter after staining with trypan blue, results for which are present in FIG. 3(a). High salt concentrations increase the osmotic pressure from its isotonic value of ~310 mOsm [17] and cause cells to lyse [13]. However, FIG. 3(a) shows that, even at the highest concentration of 0.2 M, Gd-DTPA toxicity cannot be distinguished from that of PBS within experimental error. The exposure time over the test duration of 120 mins has negligible influence on viability. Following a similar protocol, the viability of only white blood cells (WBCs) was examined. WBCs were separated from whole human blood using centrifugation and ficol separation. Their viability are presented for 30, 90 and 150 mins incubation times in FIG. 3(b). Again the toxicity of Gd-DTPA is found to be negligible compared to the PBS only sample over the duration of the experiment of 150 min.

Patterning of Blood Cells into 3D Aggregates

Next, contactless label-free in situ 3D printing of cell assemblies was demonstrated for (1) two magnetic configurations that create (a) rectangular bar and (b) three-pointed star morphologies, and (2) a magnet bank that is arranged to create whole blood spheroids of monotonically varying sizes. For the first case, the buffer solution consisted of 450 µL of 0.2M Gd-DTPA in PBS. Here, 3 µL of human whole blood was drawn and mixed with the paramagnetic buffer using a micropipette in a circular glass vial. Neodymium N52 magnets were placed in two different configurations to create a magnetic field whose strength was minimum at the center of the vial. These two configurations, presented schematically in FIG. 4, includes (1) two adjacent magnets with 180° pole angles placed side by side, and (2) three magnets with 120° pole angles placed next to each other. The configurations were also simulated based on the actual experimental design to determine the force phase portrait on cells using the Finite Element Magnetic Method (FEMM, version 4.2) in combination with MATLAB software (R2014b, The Mathworks, Inc.).

The simulations reveal that the magnetic force $F_M$ experienced by diamagnetic RBCs in the paramagnetic buffer has a single minimum value, regardless of the multiple magnet configurations employed. This single $F_M$ minimum implies that cells should converge around its spatial location, resulting in spherical assemblies. This is clearly not the case in the experiments since the simulations do not account for fluid recirculation or cell-substrate adhesion. Hence, instead of agglomerating symmetrically around the $F_M$ minimum, different 3D cell morphologies are printed due to the influence of fluid circulation. The force phase portrait, however, can foretell changes in fluid circulation associated with different magnet arrangements as seen by the vastly different phase portraits in FIGS. 4(a) and (b). Changing the magnet configuration, thus, alters the recirculation, which modifies cell transport and creates different morphologies for the 3D cell assemblies, such as the (a) bar, or (b) three pointed star. Since the final settling place of cells depend on recirculation currents, the bioprinted features will inherently have variations in its thickness. For example, the relative thickness of the 3D cell assemblies in FIG. 4(a) and (b) is conveyed qualitatively through the intensity of light passing through the features, where lighter colours is interpreted as thinner sections compared to darker thicker ones. The bar feature in FIG. 4(a) has thinner peripheries than its center, while the center section in FIG. 4(b) is thinner than its thicker peripheries, which highlight the main areas of cell settlement. Once printed in situ, the cell assemblies remain unchanged even two hours after the experiment has concluded by removing the magnets.

Other magnetic field geometries create spheroid assemblies. In the configuration of FIG. 5(a), the poles of adjacent magnets alternate to produce a spatially varying field along the cuvette that contains a whole blood suspension in 0.15 M Gd-DTPA-PBS buffer. Simply tilting the cuvette results in the formation of blood spheroids, which are separated by different sizes in situ as shown in FIG. 5(b). When the separation between a drop and the magnet that is placed below is made smaller, the magnetic field strength increases, which reduces the sizes of the whole blood spheres. The experiment was repeated three times to ensure the repeatability of spheroid formation. The variation in the sizes of different blood spheroids, of characteristic 600-1000 µm dimensions, formed with an inclination angle of ~5° at various spatial locations is shown in FIG. 5(c). For each location A-E in FIG. 5(c), the measured standard deviation of spheroid diameters are all within 5% of the average calculated diameter. This form of control over spherical cell assembly is superior to what is possible, for instance, with the hanging drop method. Since different size cell spheres are expected to have different cell densities, the in situ bioprinting method is capable of inducing mechanical stresses on a cell assembly by simply varying the magnet-cuvette separation. Subjecting a cell assembly to mechanical stress can mimic physiological conditions, which is not readily possible with conventional methods.

This method of printing 3D cell assemblies could be miniaturized to achieve better control over the resolution and smaller sizes of spheroids by either using smaller magnets or fabricating magnetic microstructures using lithographic or micromachining techniques. The microstructures could thus provide high gradient magnetic field, thus enabling patterning of cells with single cell resolution.

Patterning of Adherent Cell Lines on Tissue Culture Treated Surfaces

Figure 6:
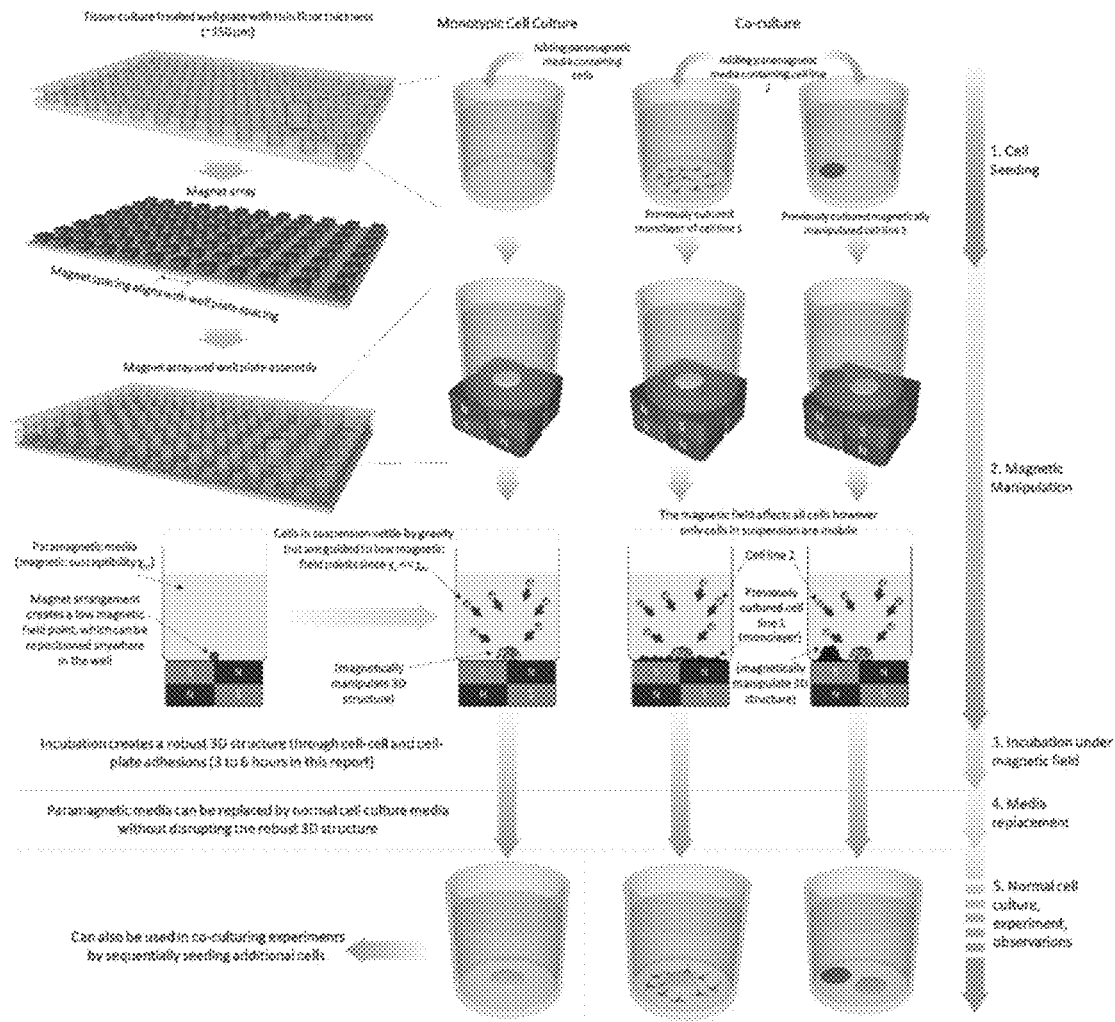
FIG. 6 shows the formation of monotypic and co-culture 3D spheroids using adherent cell lines on Tissue culture treated surfaces.

Using growth culture media Dulbecco's modified eagle medium (DMEM) supplemented with 10% Fetal Bovine Serum (FBS) and 25 mM of Gd-DTPA, the otherwise diamagnetic media is rendered paramagnetic, $\chi_m>0$, compared to that of the cell, $\chi_c<0$, i.e. diamagnetic. A magnet array is assembled and is made of 96 magnet blocks each consisting of 4 individual neodymium N52 grade 3.175 mm cube magnets. Due to the block configuration, a low magnetic field point is created, and the array spacing aligns these points within the wells of a 96 or 384 well plate. Since the difference between the magnetic susceptibility of the cell and that of the media is negative, $(\chi_c-\chi_m)<0$, a cell in suspension undergoing settling will be guided to low magnetic field points under the influence of the external magnetic field. As they aggregate in these points, and through a short incubation period of 3 to 6 hours, newly assembled cells adhere to the plate surface and each other forming robust 3D cellular structures. This allows for the safe replacement of paramagnetic media with fresh culture media, eliminating further exposure to paramagnetic salts, which can be harmful under prolonged culture conditions. [10] Such 3D structures can be created in a monotypic environment, coexist with monolayers of different cells lines, or, by altering the magnetic field, subsequent cells of the same or different type can be patterned in various positions thus allowing for adaptable co-culturing setups, as shown in FIG. 6.

Figure 7:
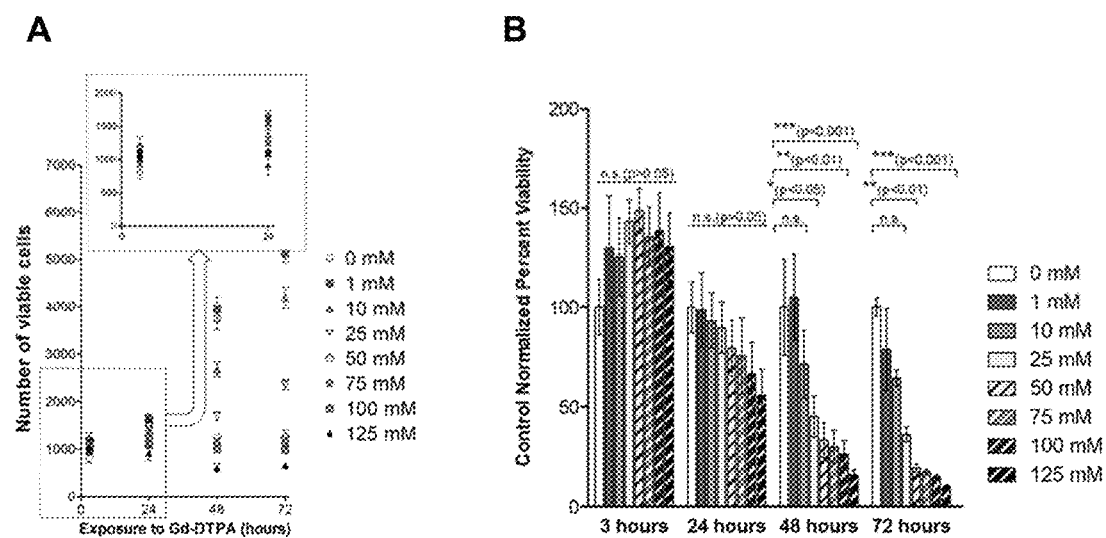
FIG. 7 shows the viability of MCF-7 cells at different concentrations of Gd-DTPA.

Effect of Gd-DTPA on Cell Viability, Cell Morphology, and Ability to Form 3D Cell Structures on Ultra-Low Adhesion and Tissue Culture Surfaces To assess limitations of Gd-DTPA for use with mammalian cells on various surfaces, cell viability was first investigated by the MTT assay for cells on a tissue culture treated surface for 1-125 mM Gd-DTPA. As the concentration of Gd-DTPA and time increases, a greater reduction in cell viability is observed, as compared to Gd-DTPA free media (0 mM Gd-DTPA) in FIG. 7(a). However, the percent viability of cells in 1-125 mM Gd-DTPA is not significant for 24 hours, as shown in FIG. 7(b). Therefore, MCF-7 cells can be exposed to Gd-DTPA up to 24 hours without imposing significant cell toxicity.

Figure 8:
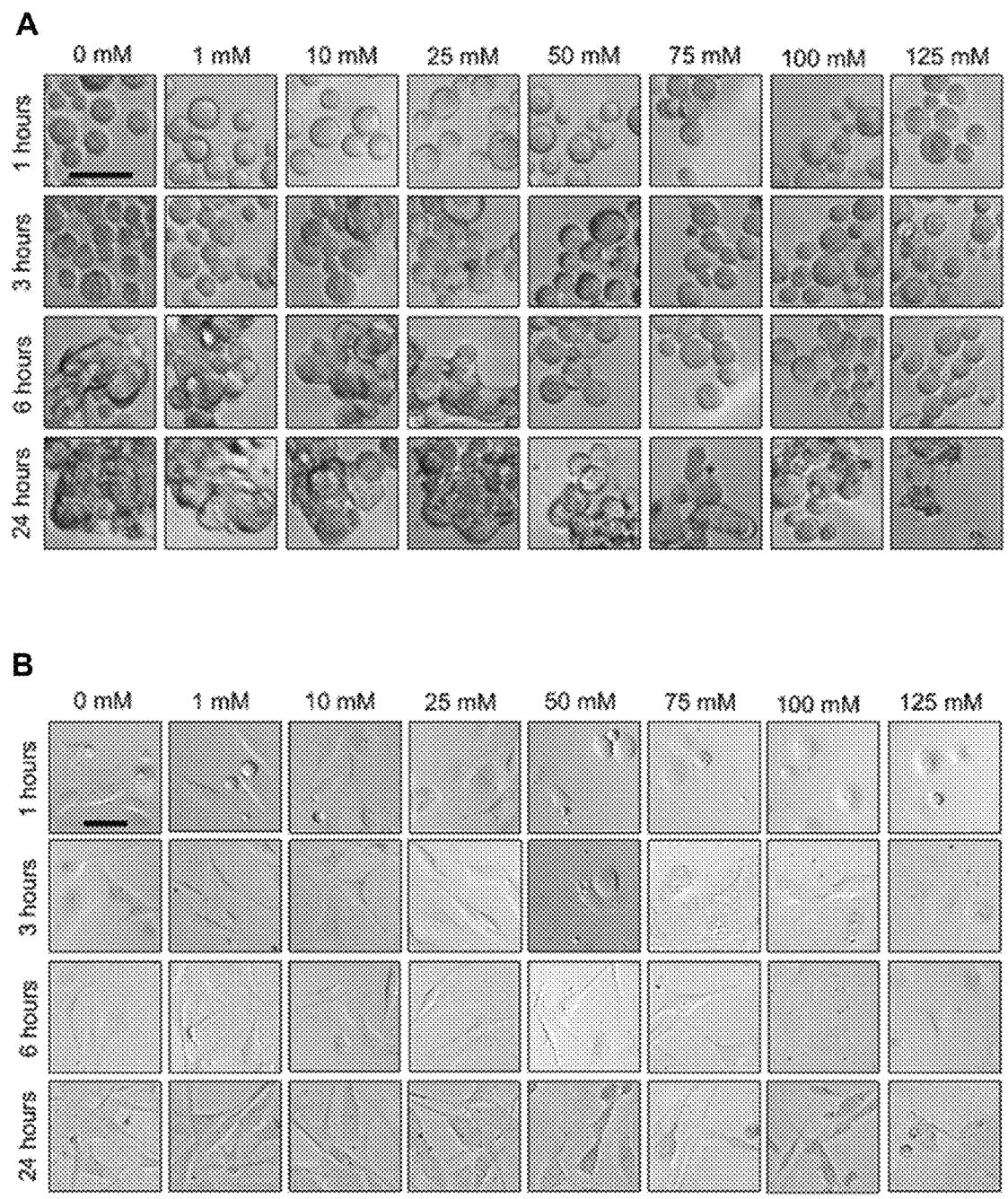
FIG. 8 shows morphology of MCF-7 cells on (a) ultra-low adhesion and (b) tissue culture-treated surfaces at different concentrations of Gd-DTPA.

To determine the effects of Gd-DTPA on cell morphology, MCF-7 cells were incubated for 24 hours in culture media suspensions containing 1-125 mM Gd-DTPA on ultra-low adhesion and tissue culture treated surfaces. For cells incubated in 1-25 mM Gd-DTPA a ultra-low adhesion surface (FIG. 8(a)), the morphology of cells up to 3 hours is indistinguishable from that of the Gd-DTPA free control. At 6 hours, evidence of cell-cell interactions is observed for Gd-DTPA concentrations of 0-25 mM. At 24 hours, evidence of cell-cell interactions is observable for all concentrations of Gd-DTPA. Therefore, since concentrations of Gd-DTPA between 1-25 mM are consistently similar to the Gd-DTPA free control, incubation of cells on ultra-low adherent surfaces is limited to 25 mM up to 24 hours. Similarly, for cells incubated on a tissue culture treated surface (FIG. 8(b)), evidence of cell adhesion (to the surface) is seen for 25 mM and below at 3 hours. At 6 and 24 hours of incubation, the cell attachment interactions overcome the effect of Gd-DTPA to prevent adhesion. Therefore, the incubation of cells suspended in Gd-DTPA is limited to 25 mM.

Figure 9:
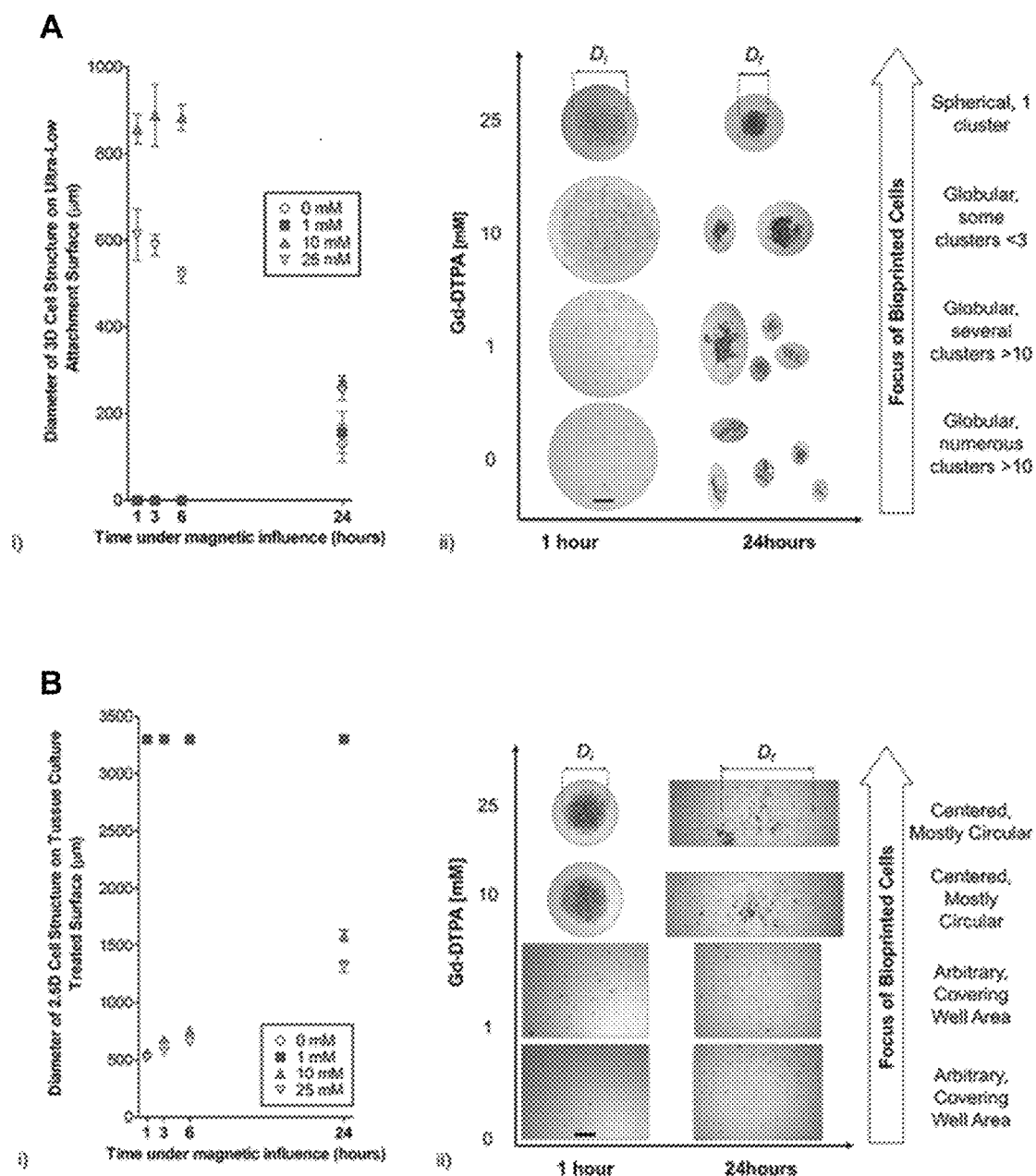
FIG. 9 shows the formation of 3D cell structures on (a) ultra-low adhesion and (b) tissue culture-treated surfaces at different concentrations of Gd-DTPA.

Next, the ability for form 3D cell structures through magnetic assistance was investigated for 0-25 mM Gd-DTPA for cells on both ultra-low adherent (FIG. 9(a)) and tissue culture treated (FIG. 9(b)) surfaces or a maximum of 24 hours. For cells suspended in a ultra-low adhesion surface, as shown in FIG. 9(a) the formation of a single, spherical cluster of cells was only observed when 25 mM is used. For all other concentrations of Gd-DTPA, including the Gd-DTPA free control, the magnetic force exerted on the cells is insufficient. Similarly, for cells suspended on a tissue culture treated surface, the use of 10 and 25 mM of Gd-DTPA forms a single 3D cell structure. However, the use of 25 mM produces a smaller effective diameter. This suggests an increase in cell-cell interactions, which is required to promote 3D cell growth. Therefore, 25 mM Gd-DTPA was used for subsequent investigations of 3D cell patterning.

Figure 10:
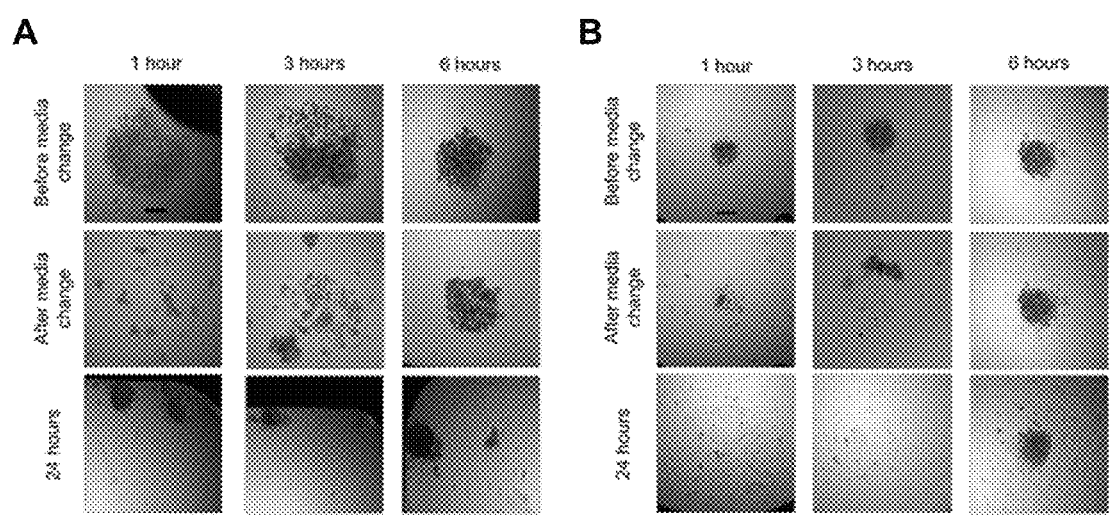
FIG. 10 shows the stability of 3D structures following culture medium changes to remove Gd-DTPA following cell patterning.

Stability of 3D Structures Following Culture Medium Changes to Remove Gd-DTPA Following Cell Patterning As shown in FIG. 10, 3D cell structures are formed within 1 hour of incubation using 25 mM Gd-DTPA. However, the 3D cell structure is not stable when the patterned cell suspension is interrupted by necessary culture medium changes with Gd-DTPA free medium to prevent over-exposure to Gd-DTPA at 1 and 3 hours. However, at 6 hours, the 3D cell structure is maintained before and after culture media washes. This is seen for 3D cell structures formed on (a) ultra-low adhesion and (b) tissue culture treated surfaces. This correlates to the evidence of cell-cell interactions required for 3D cell structure formation seen in the morphology analysis. Therefore, 6 hours of incubation using 25 mM Gd-DTPA is required for 3D cell patterning of MCF-7 cells on both ultra-low adhesion and tissue culture treated surfaces.

Visualization of Viability and Dimensions of 3D Cell Structures Formed With and Without Magnetic Assembly on Various Surfaces Relative viability (i) and dimensions (ii) of 4 cell structures is observed: (FIG. 11(a)) 3D cell structures formed via magnetic assembly on ultra-low adhesion; (FIG. 11(b)) 2.5D structures formed via magnetic assembly on tissue culture treated surfaces; (FIG. 11(c)) self-assembled 3D cell structures formed on round-bottom ultra-low attachment surfaces without magnetic assistance, and (FIG. 11(d)) spontaneously-formed spheroids formed on flat-bottom ultra-low surfaces formed without magnetic assistance. The resulting structures are: a single 3D cell structure, a 3D cell structure and a simultaneous 2D monolayer, a 3D cell structure (2.5D cell structure), and multiple 3D cell structures for FIG. 11(a-d), respectively. For viability, dead cells are shown as green, while live cells are shown as blue. Dimensions are measured at 6, 24, 48, and 72 hours using a box-and-whisker plot at the $25^{th}$, $50^{th}$, and $75^{th}$ percentiles, with upper and lower whiskers reaching the $95^{th}$ and $5^{th}$ percentile measurements, respectively. When comparing magnetically-assembled 3D cell structures and 3D self-assembled cell structures, the distribution of area measurements is smaller for those formed through magnetic assembly. In addition, for the formation of a 2.5D and 3D cell structures by magnetic assistance, the area measurements consistently display a normalized distribution. For spontaneously-formed 3D cell structures without magnetic assistance, numerous 3D cell structures are produced, with little control of individual 3D structure dimensions.

Figure 11:
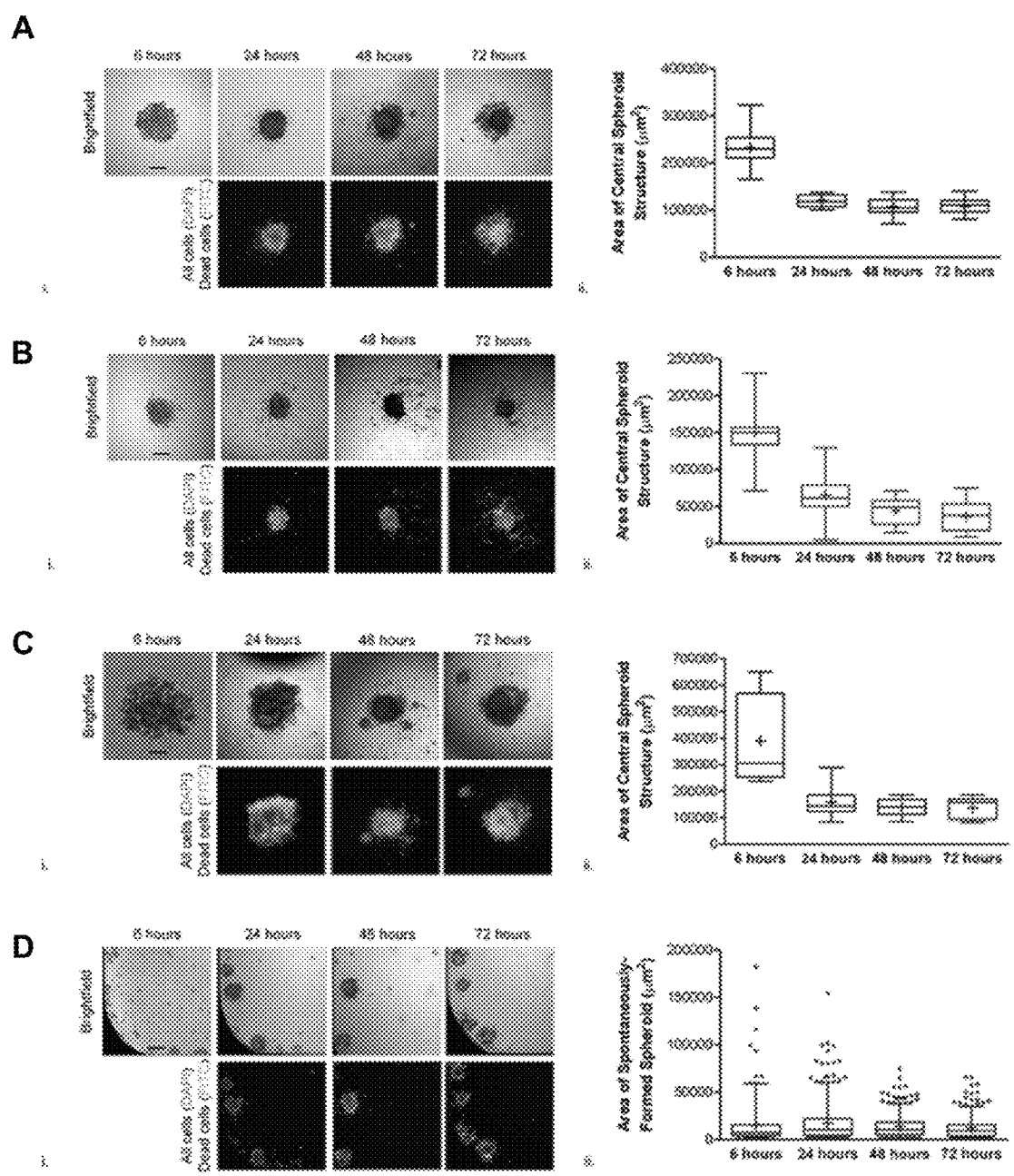
FIG. 11 shows visualization of viability and dimensions of 3D cell structures formed via magnetic assembly on (a) ultra-low adhesion and (b) tissue culture treated surfaces, as well as those formed sans magnetic assistance on (c) round-bottom and (d) flat-bottom ultra-low adhesion surfaces.
Figure 12:
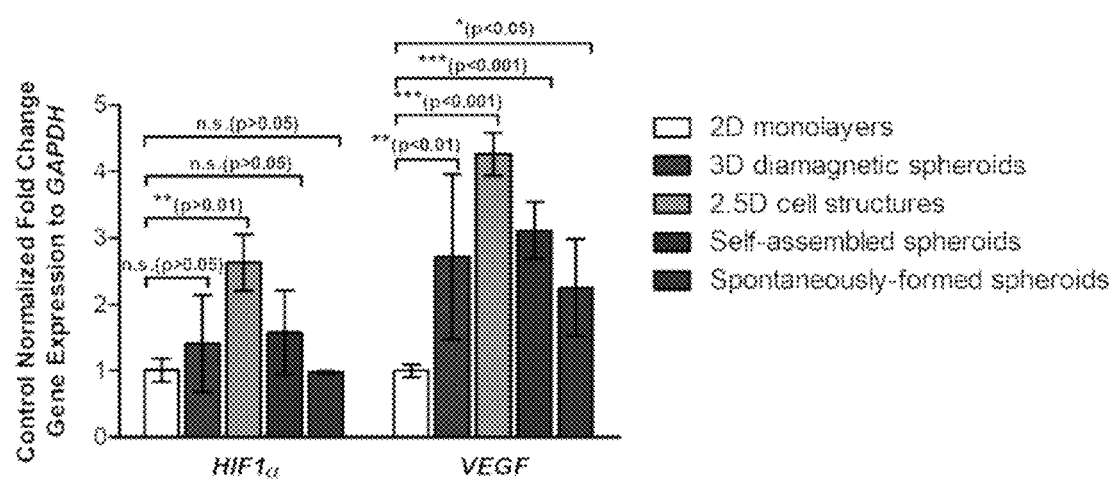
FIG. 12 shows the relative gene expression of cell structures formed via magnetic assembly on ultra-low adhesion cell and tissue culture treated surfaces, as well as those formed sans magnetic assistance on round-bottom and flat-bottom ultra-low adhesion surfaces.

Relative Gene Expression of 3D Cell Structures Formed With and Without Magnetic Assembly on Various Surfaces The control normalized fold change gene expression to glyceraldehyde 3-phosphate dehydrogenase (GAPDH) in 2D monolayers of hypoxia inducible factor-1 alpha (HIF1α) and vascular endothelial growth factor (VEGF) is assessed for the four 3D cell structures mentioned in FIG. 11. Expression of these genes is used to assess the stresses associated with formation of the various structures and is expected to be over expressed for all cell structures, as shown in FIG. 12. For HIF1α, the overexpression of 3D diamagnetic cell structures, 3D self-assembled cell structures, and spontaneously formed 3D cell structures is not significant. This is likely due to the small dimensions of the 3D cell structures, which do not promote hypoxia. The over-expression of HIF1α in the 2.5D magnetically formed cell structures is likely due to the actively proliferating 2D monolayer. VEGF is significantly overexpressed for all 3D cell structures.

Co-Culture Capability of Contactless Magnetic Cell Manipulation

Figure 13:
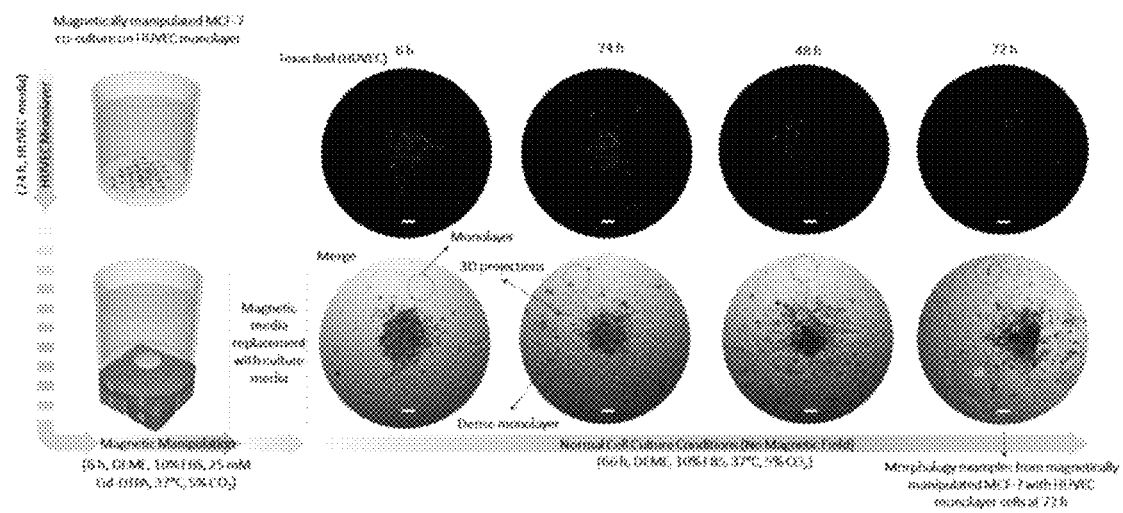
FIG. 13 shows the magnetic manipulation of MCF-7 and HUVEC co-culture
Figure 13:
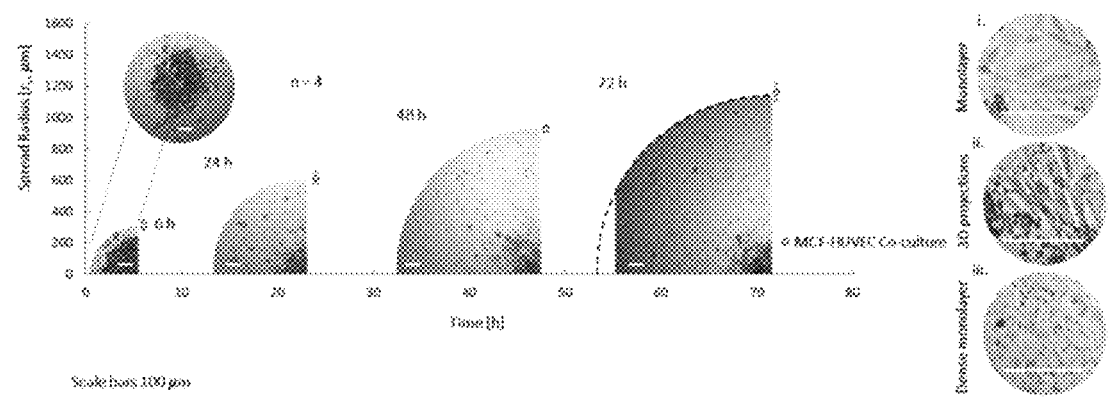

The co-culture capability of the method was demonstrated where magnetically manipulated MCF-7 cells are cultured in the presence of a HUVEC monolayer for 3 days. In this case, 5,000 red fluorescent protein positive (RFP+) HUVECs are seeded and cultured for 24 h in a 384 TCT well plate in the presence of HUVEC culture media. Subsequently, the media is removed, and replaced with paramagnetic media. The well plate is then placed on a magnetic array. 2,000 MCF-7 cells are then seeded and incubated for 6 hours, after which the media is replaced with fresh Gd-DTPA free culture media (DMEM, 10% FBS) and left to incubate until t=72 h. Although HUVECs are subjected to the same magnetic force that is used to focus the MCF-7 into a central structure, their adhesion to the well floor allows them to remain stationary. Thus only the MCF-7 cells, which are still in suspension undergo diamagnetophoresis and form a central structure. In FIG. 13(a), it can be seen that at t=6 h, magnetically focused MCF-7 cells have caused a localization of HUVECs in the same area. This may be due to cell-cell interactions between the two cell lines at the low magnetic field point. Monolayer MCF-7 cells can also be seen surrounding the central cellular structure, while other monolayer HUVECs are scattered throughout the field of view. At t =24 h, evidence of 3D cell projections and dense monolayer cells are highlighted in yellow and cyan dashed lines respectively. At t=48 h, cells continue their radial spread, and while more dense monolayer patches are seen 3D projections do not share the same growth. At t=72 h, dense monolayer regions continue to merge and grow while 3D projection appear to have remained relatively the same size as the previous time point. Such densely packed regions of cells seem to be devoid of HUVECs, which continually reduce in numbers at the expense of an advancing MCF-7 front.

The central focusing of cells using magnetic fields provides a further dimension of analysis to the cell culture conditions through the measure of the cell spread progression. The spread of cells in this case provides information about their mobility, given environmental conditions, and is evaluated by measuring the diameter of the rim created by the monolayer cells at the outskirts of the cell spread, see FIG. 13(b) depicts the spreading of magnetically manipulated MCF-7 cells with the presence of a HUVEC monolayer over a period of 72 h, which is appear to be quasi linear.

Sequential Co-Culture Capability of Contactless Magnetic Cell Manipulation

Figure 14:
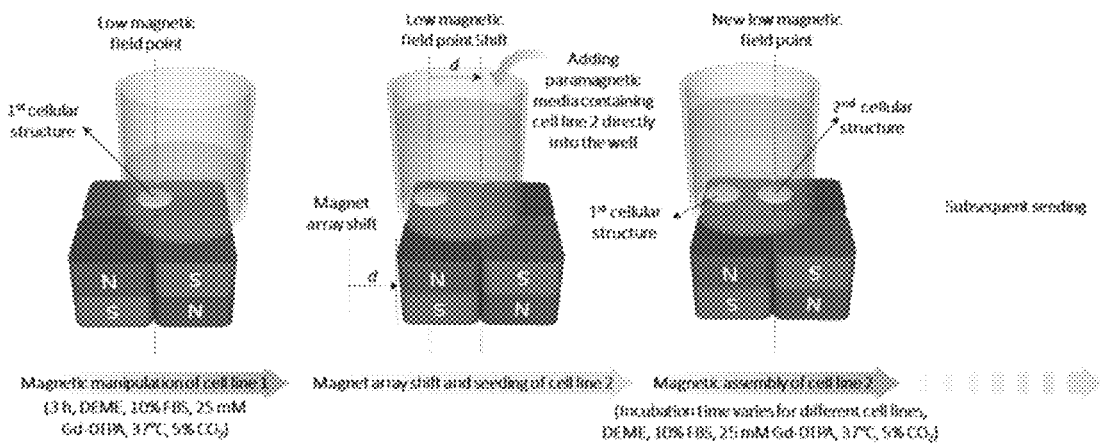
FIG. 14 shows sequential magnetic manipulation of cells on tissue culture treated surfaces.
Figure 14:
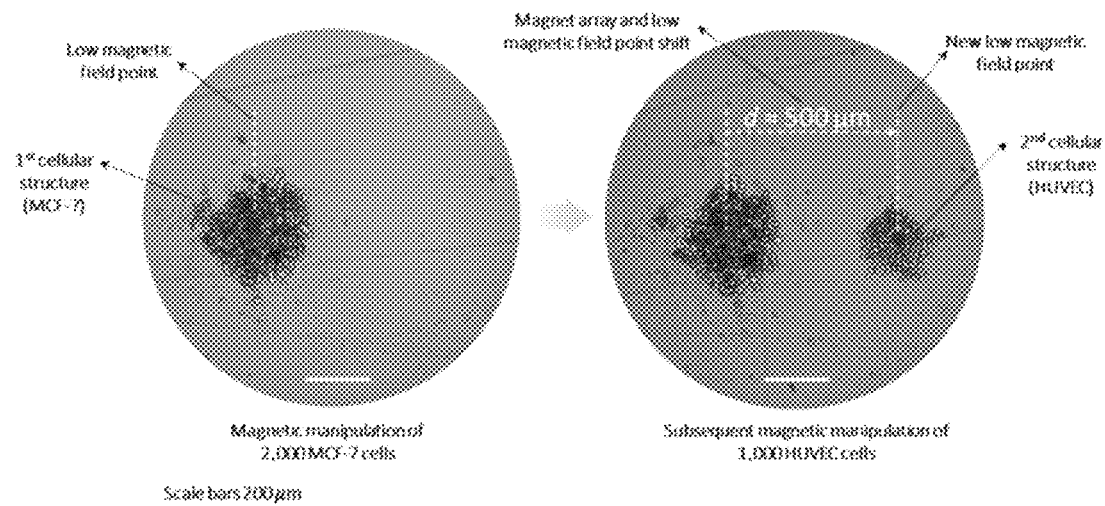

To showcase further cell manipulation capability, cell co-culture was performed where two subsequent magnetic cell manipulations of different cell line in the same well forming two individual central cellular structures, see FIG. 14(a). Firstly, 2,000 MCF-7 cells are incubated for 3 h in paramagnetic media and under influence of a magnetic field forming an initial central cellular structure. Subsequently, and without a media change, paramagnetic media containing 1,000 HUVEC cells is then added to the well. By shifting the magnetic array a distance of d≈500 the low magnetic field point is repositioned with reference to the well. The shift causes the MCF-7 cells to be off-centered with reference to the new low magnetic field point and thus are subject to a body force in its direction. However, they remain stationary due their cell-cell and cell-plate adhesions. Therefore, only the HUVEC cells, which are in suspension, are able to settle into a new central cellular structure governed by the new magnetic field, see FIG. 14(b). Such cell positioning technique can thus be used to examine collocated populations of various cell types and their interactions.

The previous non-limiting examples are illustrative of the present application. While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety.

FULL CITATIONS FOR DOCUMENTS REFERRED TO IN THE APPLICATION

1. Tasoglu, S. and U. Demirci, *Bioprinting for stem cell research*. Trends in biotechnology, 2013. 31(1): p. 10-19.

2. Mehrishi, J. N. and J. Bauer, *Electrophoresis of cells and the biological relevance of surface charge*. Electrophoresis, 2002. 23(13): p. 1984-1994.

3. Korohoda, W. and A. Wilk, *Cell electrophoresis—a method for cell separation and research into cell surface properties*. Cellular and Molecular Biology Letters, 2008. 13(2): p. 312-326.

4. Augustsson, P., et al., *Iso-acoustic focusing of cells for size-insensitive acousto-mechanical phenotyping*. Nature communications, 2016. 7.

5. Nordin, M. and T. Laurell, *Two-hundredfold volume concentration of dilute cell and particle suspensions using chip integrated multistage acoustophoresis*. Lab on a Chip, 2012. 12(22): p. 4610-4616.

6. Xu, C., et al., *Study of Droplet Formation Process during Drop-on-Demand Inkjetting of Living Cell-Laden Bioink*. Langmuir, 2014. 30(30): p. 9130-9138.

7. Kimura, T., et al., *Micropatterning of cells using modulated magnetic fields*. Langmuir, 2005. 21(3): p. 830-832.

8. Winkleman, A., et al., *A magnetic trap for living cells suspended in a paramagnetic buffer*. Applied physics letters, 2004. 85(12): p. 2411-2413.

9. Durmus, N. G., et al., *Magnetic levitation of single cells*. Proceedings of the National Academy of Sciences, 2015. 112(28): p. E3661-E3668.

10. Akiyama, Y. and K. Morishima, *Label-free cell aggregate formation based on the magneto-Archimedes effect*. Applied Physics Letters, 2011. 98(16): p. 163702.

11. Fattah, A. R. A., S. Ghosh, and I. K. Puri, *High Gradient Magnetic Field Microstructures for Magnetophoretic Cell Separation*. Journal of Chromatography B, 2016.

12. Shen, F., et al., *Label-free cell separation using a tunable magnetophoretic repulsion force*. Analytical chemistry, 2012. 84(7): p. 3075-3081.

13. Melville, D., F. Paul, and S. Roath, *Fractionation of blood components using high gradient magnetic separation*. IEEE Transactions on Magnetics, 1982. 18(6): p. 1680-1685.

14. Melville, D., F. Paul, and S. Roath, *Direct magnetic separation of red cells from whole blood.* 1975.

15. Morgunov, R. B., et al., *Thermally-induced paramagnetism of spiropyrane iodides*. New Journal of Chemistry, 2009. 33(6): p. 1374-1379.

16. Tsutsui, H. and C. -M. Ho, *Cell separation by non-inertial force fields in microfluidic systems*. Mechanics research communications, 2009. 36(1): p. 92-103.

17. Graham, M., *Comparison of volume and surface mechanisms for magnetic filtration of blood cells*. Le Journal de Physique Colloques, 1984. 45(C1): p. C1-779-C1-784.

The invention claimed is:

1. A method of forming an assembly of particles in a plurality of receptacles, the method comprising:
combining a plurality of diamagnetic particles with a paramagnetic agent to form a suspension of particles in paramagnetic solutions in the plurality of receptacles, the diamagnetic particles including cells; and
applying external magnetic fields to the suspension of particles in the paramagnetic solutions to form one or more regions of lower magnetic field strength, the external magnetic fields being provided by aligning an array of magnet arrangements with the plurality of receptacles,
wherein the diamagnetic particles in the suspensions move towards the one or more regions of lower magnetic field strength forming the assembly of particles.

2. The method of claim 1, wherein the assembly of particles forms a 3-dimensional structure or aggregate.

3. The method of claim 2, wherein the 3-dimensional structure is a spheroid or sphere, and the magnet arrangements include a two-dimensional array of magnets, wherein poles of aadjacent magnets alternate in the magnet arrangements.

4. The method of claim 2, wherein the 3-dimensional structure comprises a bar, a polyhedron or a curved shape.

5. The method of claim 1, wherein the array of magnet arrangements are integral with the plurality of receptacles or located under the array of magnet arrangements.

6. The method of claim 5, wherein the receptacles are wells.

7. The method of claim 5, wherein the receptacles comprise surfaces that are treated to reduce or promote cell adhesion.

8. The method of claim 1, wherein the paramagnetic agent comprises a Gadolinium based salt or contrasting agent.

9. The method of claim 8, wherein the paramagnetic solution comprises the Gadolinium based salt or the contrasting agent mixed with phosphate-buffered saline or cell culture media.

10. The method of claim 1, wherein the cells are adherent cells or non-adherent cells, the cells are of a same cell type or different cell types.

11. The method of claim 1, wherein the particles in the suspension form a first aggregate in the receptacles and the method further comprises adding a second plurality of particles to the receptacles and applying external magnetic fields to suspensions comprising the second plurality of particles in the paramagnetic solution to form a second aggregate of particles.

12. The method of claim 11, wherein the first aggregate and the second aggregate of particles are spatially resolved, or wherein the first aggregate and the second aggregate of particles form a 3-dimensional layered structure.

13. The method of claim 1, wherein the receptacles comprise an adherent monolayer cell culture.

14. The method of claim 1, comprising applying the external magnetic fields to the suspension of cells in the paramagnetic solutions for at least 4 hours, at least 5 hours, or at least 6 hours.

15. The method of claim 1, further comprising replacing all or part of the paramagnetic solution with growth media that does not contain the paramagnetic agent.

16. The method of claim 2, wherein the 3-dimensional structure or aggregate comprises a spheroid or a sphere.

17. The method of claim 6, wherein the receptacles comprise flat bottom surfaces.

18. The method of claim 6, wherein the receptacles are wells on a micro-titer plate or a cell culture plate.

19. The method of claim 13, wherein the plurality of cells is in a monolayer of cells on bottom surfaces of the receptacles.

20. The method of claim 14, wherein the method comprises applying the external magnetic fields to the suspension of cells in the paramagnetic solutions for between about 3 hours and 8 hours.

21. The method of claim 8, wherein the paramagnetic agent comprises a Gadolinium-diethylenetriamine pentaacetic acid (Gd-DTPA).

22. The method of claim 21, wherein the concentration of Gd-DTPA in the paramagnetic solution is between about 0.001 M to 0.2 M.

* * * * *